United States Patent [19]

Bledsoe et al.

[11] Patent Number: 4,955,369

[45] Date of Patent: Sep. 11, 1990

[54] DYNAMICALLY SHIFTABLE COUNTER SHEAR FORCE KNEE BRACE

[76] Inventors: Gary R. Bledsoe, 316 Clayton, Grand Prairie, Tex. 75052; Brett O. Bledsoe, 2509 Corkwood Pl., Arlington, Tex. 76017

[21] Appl. No.: 263,065

[22] Filed: Oct. 27, 1988

[51] Int. Cl.$^5$ .............................................. A61F 5/04
[52] U.S. Cl. .................................... 128/80 C; 128/88
[58] Field of Search .................. 128/80 C, 80 F, 88

[56] References Cited

U.S. PATENT DOCUMENTS

| | | | |
|---|---|---|---|
| 3,046,981 | 7/1962 | Biggs Jr. et al. | 128/80 C |
| 4,220,148 | 9/1980 | Lehneis | 128/80 C |
| 4,361,142 | 11/1982 | Lewis et al. | 128/80 |
| 4,370,977 | 2/1983 | Mauldin et al. | 128/80 |
| 4,379,463 | 4/1983 | Meier et al. | 128/80 |
| 4,381,768 | 5/1983 | Erichson et al. | 128/80 C |
| 4,487,200 | 12/1984 | Feanny et al. | 128/80 |
| 4,506,661 | 3/1985 | Foster | 128/80 C |
| 4,554,913 | 11/1985 | Womack et al. | 128/80 C |
| 4,556,053 | 12/1985 | Irons | 128/88 |
| 4,573,455 | 3/1986 | Hoy | 128/88 |
| 4,624,247 | 11/1986 | Ford | 128/80 |
| 4,632,097 | 12/1986 | Brooks | 128/88 |
| 4,633,867 | 1/1987 | Kausek et al. | 128/88 |
| 4,635,623 | 1/1987 | Charuest et al. | 128/80 |
| 4,649,906 | 3/1987 | Spademan | 128/80 |
| 4,697,583 | 10/1987 | Mason et al. | 128/80 |
| 4,699,129 | 10/1987 | Aaserade et al. | 128/80 C |
| 4,723,539 | 2/1988 | Townsend | 128/80 C |
| 4,765,318 | 8/1988 | Tranberg et al. | 128/80 C |
| 4,781,180 | 11/1988 | Solomonow | 128/80 |
| 4,791,916 | 12/1988 | Paez | 128/88 |
| 4,793,333 | 12/1988 | Marquette | 128/80 C |
| 4,803,975 | 2/1989 | Meyers | 128/80 C |
| 4,805,606 | 2/1989 | McDavid | 128/80 C |
| 4,817,588 | 4/1989 | Bledsoe | 128/80 C |

FOREIGN PATENT DOCUMENTS 1024204 2/1958 Fed. Rep. of Germany .... 128/80 C

OTHER PUBLICATIONS

1982 Medical Technology Inc., "Application Instructions".

Primary Examiner—Edgar S. Burr
Assistant Examiner—Tonya Lamb
Attorney, Agent, or Firm—Hubbard, Thurman, Turner, Tucker & Harris

[57] ABSTRACT

A dynamically shiftable knee brace is used to counteract anterior tibial displacement caused during leg extension by the quadriceps muscle when the anterior cruciate ligament is missing or damaged. The brace includes pairs of rigid thigh and calf support members which extend along and are strapped to thigh and calf portions of the leg, the support member pairs being pivotally connected at their inner ends to one another by a pair of specially designed hinges positioned on opposited sides of the knee. As the leg is extended from a flexed position toward its fully straightened position the hinges cause a relative anterior-posterior shift between the support member pairs in a manner creating a shear force across the knee which is opposite that generated by the quadriceps muscle. The connection strap system is operative to substantially prevent distal brace shift along the leg, and may also be adjusted to cause selective lateral or medial flexion of the calf support members relative to the thigh support members in response to leg extension.

18 Claims, 4 Drawing Sheets

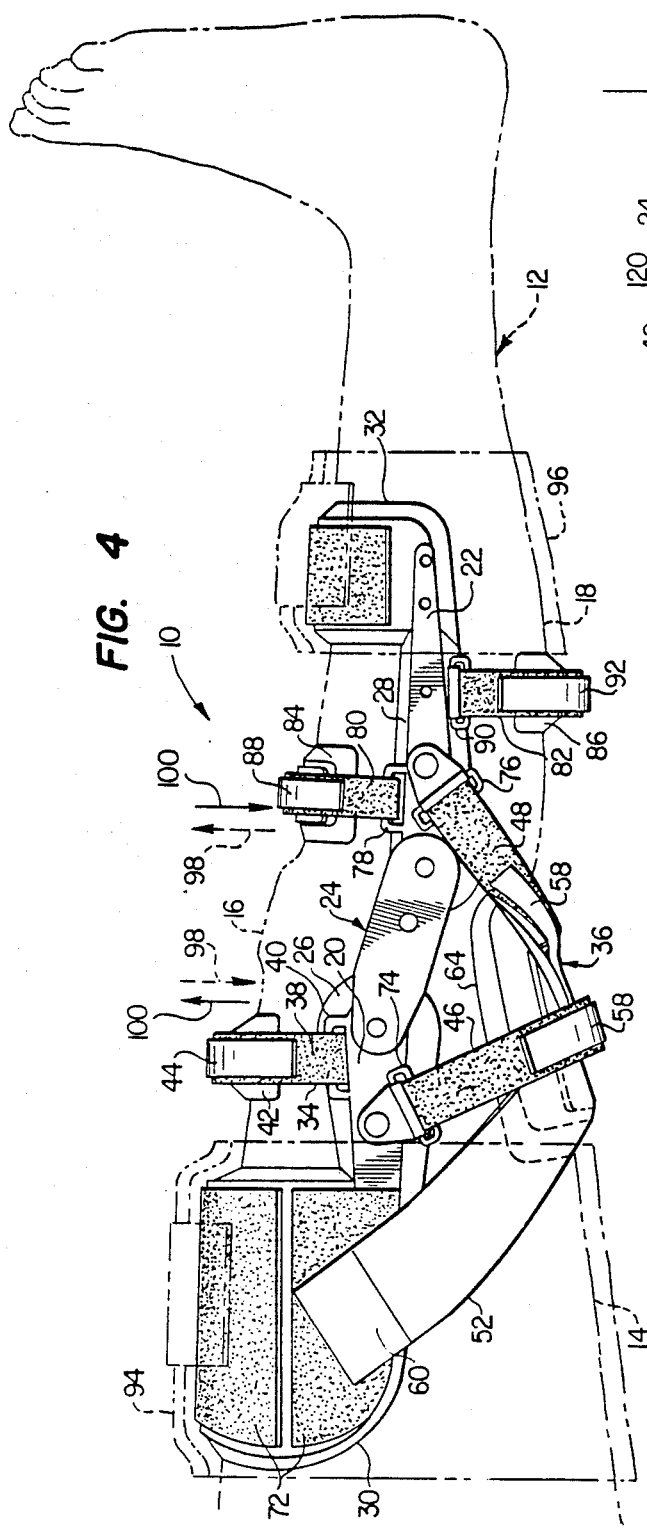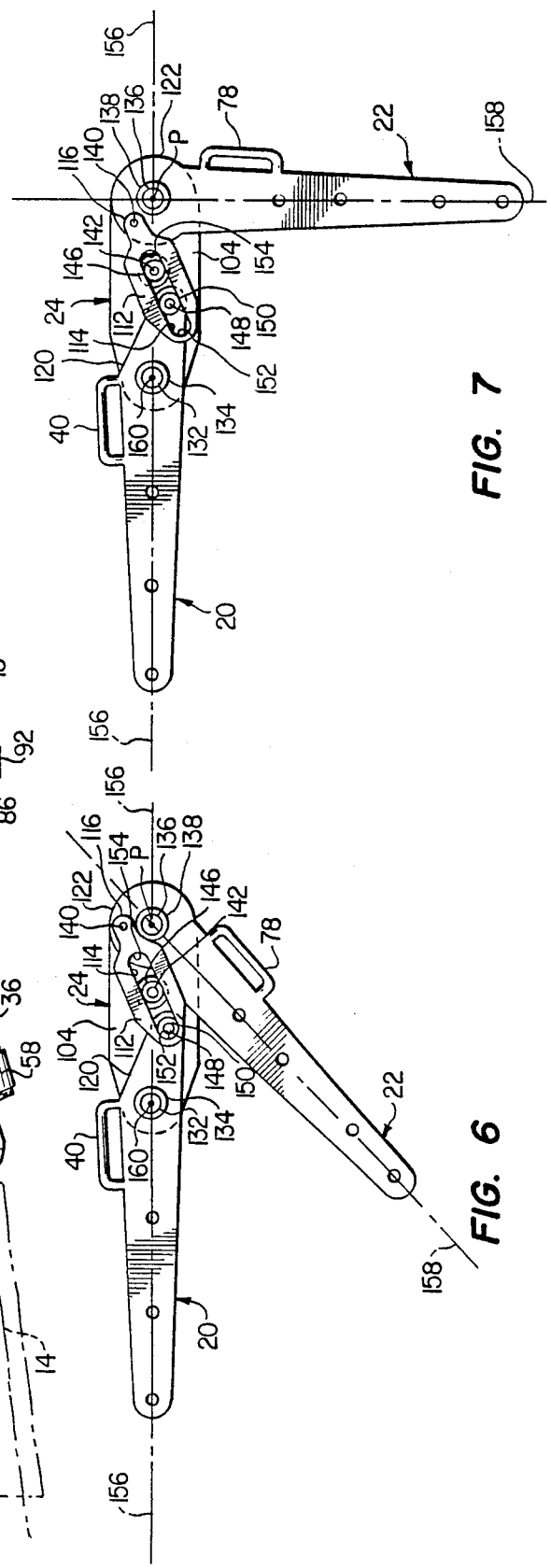

DYNAMICALLY SHIFTABLE COUNTER SHEAR FORCE KNEE BRACE

BACKGROUND OF THE INVENTION

The present invention relates generally to orthopedic appliances and, in a preferred embodiment thereof, more particularly provides a uniquely operative knee brace whose thigh and calf support structures are caused to laterally shift relative to each other, in response to extension and flexion of the leg, to controllably counteract the tibial shifting forces caused by the absence of or damage to the anterior cruciate ligament.

During extension of the normal human leg toward its fully straightened position the anterior shifting force imposed on the tibia caused by the quadriceps muscle is counteracted by the anterior cruciate ligament to prevent the tibia from being anteriorly shifted away from its normal position relative to the femur. Loss of or damage to the anterior cruciate ligament permits the quadriceps muscle to cause this undesirable tibial shift unless a counteractive force is imposed on the tibia by alternate means such as orthopedic appliance.

An example of a conventional attempt to artificially create this counteractive force is represented by the anterior cruciate ligament brace disclosed in U.S. Pat. No. 4,697,583 to Mason et al. In the Mason et al knee brace, a four-point static leg load system is used in an attempt to maintain a posteriorly directed resultant force on the tibia, while at the same time maintaining an anteriorly directed resultant force on the femur, the two resultant forces creating a counteractive shear force across the knee which is oppositely directed relative to the tibia-femur shear force across the knee created by the quadriceps muscle as the leg is extended toward its straightened position.

To achieve this four-point leg loading format, the Mason et al brace utilizes a pair of rigid thigh support members which extend along opposite sides of the thigh, and a pair of rigid calf support members which extend along opposite sides of the calf. The inner ends of the thigh support members are pivotally connected to the inner ends of the calf support members by a pair of polycentric hinges, positioned on opposite sides of the knee, whose pivotal motions are designed to closely mimic that of the human knee joint.

A generally U-shaped anterior thigh cuff member is secured to the outer ends of the thigh support members, and a generally U-shaped posterior calf cuff member is secured to the outer ends of the calf support members. A posterior thigh force strap is interconnected between the thigh support members and is positioned longitudinally between the anterior thigh cuff member and the hinges. In a similar fashion, an anterior tibial force strap is interconnected between the calf support members and is positioned longitudinally between the posterior calf cuff member and the hinges.

With the leg in its fully extended position, the Mason et al brace is installed by first aligning the hinges on opposite sides of the knee, with the thigh and calf support members respectively extending along opposite sides of the thigh and calf. The thigh and calf force straps are then respectively tightened against the back of the thigh and the front of the tibia.

The tightening of these two straps sets up two three-point force sets along the leg—the first force set comprising the posteriorly directed forces from the anterior cuff and strap members which oppose the anteriorly directed force from the posterior strap, and the second force set comprising the anteriorly directed forces from the posterior strap and cuff members which oppose the posteriorly directed force from the anterior strap. As a result, with the leg in its extended position, the two force straps cooperate to create a shear force across the knee joint which is directly opposite that created by the quadriceps muscle This counter shear force created by the posterior thigh and anterior tibia straps in the Mason et al brace is static. The force is greatly limited and cannot appreciably change as the leg is flexed or extended. Thus the straps cannot compensate for the increased tibial displacement force caused by the quadriceps muscle as the leg is extended. The direction of force of the two straps, when the leg is flexed at 90°, tends to cause the entire brace structure to be undesirably shifted distally along the leg such that the brace must frequently be tugged upwardly to keep it in place. This, of course, decreases the wearing comfort of the brace and markedly decreases its effectiveness as a mechanical substitute for a missing or damaged anterior cruciate ligament. Attempts have been made to frictionally inhibit this distal shifting of the brace by securing it to a tubular undersleeve formed from a resilient material. However, in actual use it has been found that the brace still tends to distally migrate downwardly along the leg in response to flexure thereof.

Another problem associated with this type of statically loaded brace is that it does not accurately track (in a reverse sense) the quadriceps muscle-induced shear force across the knee joint. Specifically, the quadriceps muscle creates this shear force beginning at a leg flexion angle of approximately 40° and significantly increases the force as the leg is moved closer and closer toward its fully extended position. With the leg between its fully flexed position and a flexion angle of approximately 40°, however, the quadriceps muscle exerts only a relatively slight anterior displacement force on the tibia. In contrast, the Mason et al brace creates an almost static shear force across the knee joint which actually increases slightly as the leg is flexed. This is contrary to the required force, which should increase as the leg extends. At best, therefore, this type of conventional brace only provides a minimal amount of the counter shear force of the anterior cruciate ligament which it is designed to replace or supplement.

In view of the foregoing it is an object of the present invention to provide a knee brace which eliminates or minimizes the above-mentioned and other limitations and disadvantages associated with conventional brace structures intended to function as an artificial anterior cruciate ligament.

SUMMARY OF THE INVENTION

In carrying out principles of the present invention, in accordance with a preferred embodiment thereof, an improved knee brace is provided which functions in a unique manner to counteract the undesirable quadriceps muscle-induced anterior translation of the tibia, in the absence of or damage to the anterior cruciate ligament, as the leg is extended from a flexed position toward its straightened position. This tibial translation force, which creates an anterior-posterior shear force across the knee joint during leg extension, occurs primarily within the 40°-0° angular leg flexion range, reaching an appreciable level at about 40° leg flexion and increasing as the leg flexion angle is further reduced.

To counteract this shear force, thigh and calf portions of the improved brace are caused to shift relative to one another, in an anterior-posterior sense, in response to leg extension in a manner dynamically creating (i.e., in response to leg extension force) an oppositely directed shear force across the knee joint at a force level closely proportional, in a reverse sense, to that imposed by the quadriceps muscle throughout the leg flexion.

In a preferred embodiment thereof, the improved knee brace of the present invention comprises rigid thigh support means positionable along lateral and medial sides of the thigh, rigid calf support means positionable along lateral and medial sides of the calf, and attachment means for operatively attaching the thigh and calf support means to the leg and transmitting anterior and posterior forces from the thigh and calf support means to the leg.

The thigh and calf support means are pivotally interconnected by hinge means positionable on opposite sides of the knee and uniquely operative to create, as the leg is extended through its 75° flexion position toward its fully straightened position, an increasing relative anterior-posterior shifting between the thigh and calf support means in a manner creating the aforementioned counter shear force across the knee joint. By initiating this unique brace "shift" at a leg flexion angle of approximately 75°, by the time the leg reaches a flexion angle of approximately 40° the soft tissue "give" in the thigh and calf is taken up and the brace shifting forces are more efficiently transferred to the femur and tibia, thereby closely tracking, in a reverse sense, the quadriceps muscle-induced shear force across the knee in the critical 40°-0° leg flexion range.

According to another feature of the present invention, the attachment means include a specially designed posterior thigh strap network which comprises an adjustably tightenable posterior force strap connected at its outer ends to opposite side portions of the thigh support means, extending around the underside of the thigh, and carrying a thigh pad which bears against the thigh; a pair of adjustably tightenable control straps interconnected between the force strap and opposite side portions of the calf support means forwardly of the force strap; and a pair of elastic retraction straps interconnected between the force strap and opposite rear side portions of the thigh support means.

As the leg is extended, the resulting pivotal motion of the calf support means tensions the control straps and forwardly moves the force strap, and the thigh pad which is pressed against the thigh, along the thigh while forwardly stretching the elastic retraction straps. When the leg is subsequently flexed, the stretched elastic retraction straps assist in rearwardly moving the force strap and its associated thigh pad back their original positions along the underside of the thigh.

Importantly, it has been found that this unique forward and rearward movement of the thigh pad varies the location along the thigh at which the brace's anterior shifting force is transmitted to the leg, thus increasing leverage of the brace as the leg is extended. This forward and rearward movement of the thigh pad also mimics stretching of the skin and muscle of the posterior thigh in a manner essentially precluding distal brace migration along the leg in response to extension and flexion thereof.

The control strap portion of the posterior strap network also permits the brace to be used to counteract undesirable lateral-medial displacement of the tibia during leg extension. Specifically, by simply tightening one control strap more than the other when the brace is initially installed on the leg, extension of the leg tensions the tighter control strap first to thereby selectively laterally or medially flex the calf support means relative to the thigh support means and counteract tibial displacement in the opposite lateral-medial direction.

In the preferred embodiment of the improved brace the attachment means also include an adjustably tightenable tibial force strap which is secured at its opposite ends to opposite side portions of the calf support means and extends along and bears against the anterior side of the calf to transfer posterior brace shifting force thereto. By adjusting this force strap the amount of anterior-posterior brace shifting force transmitted to the leg can be easily varied.

The knee brace of this invention is conveniently attachment means adjustably tightened, with the leg in an approximately 90° flexion position. This advantageously facilitates installation of the brace on the leg. As previously described, the reduction in counter shear force when the leg is at this 90° flexion angle helps to eliminate distal brace migration along the leg.

BRIEF DESCRIPTION OF THE DRAWINGS

FIG. 4 is a view similar to that in FIG. 3, but with the leg moved to its fully extended position;

FIGS. 6-11 are assembled side elevational views of the hinge and support member structure shown in FIG. 5, with the front hinge cover plate removed for illustrative clarity, and sequentially illustrate the operation of the hinge as the support members are pivoted between their fully flexed position in FIG. 6 to their fully extended position in FIG. 11.

DETAILED DESCRIPTION

Figure 1:
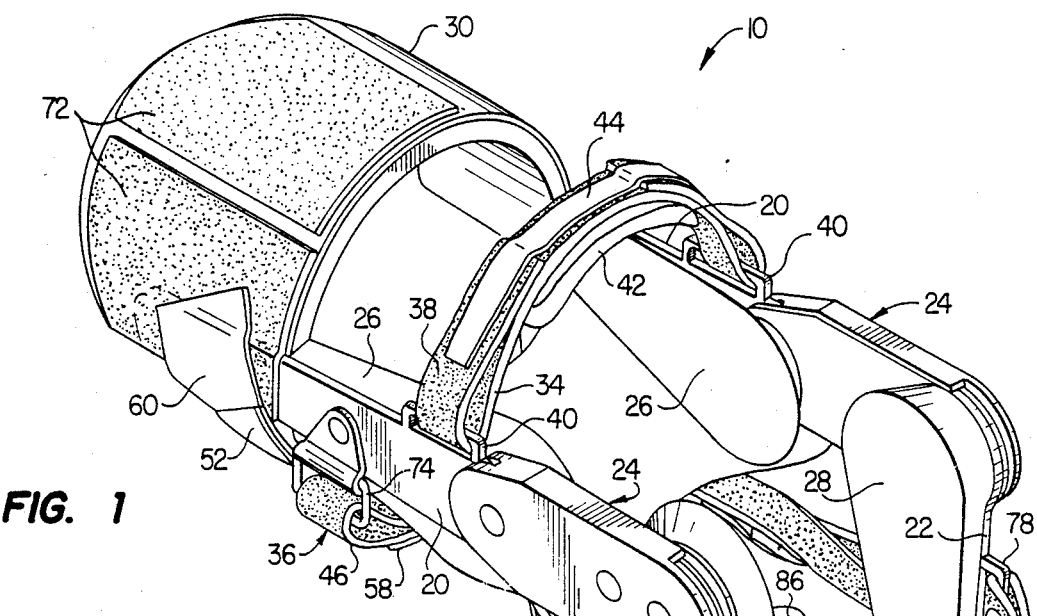
FIG. 1 is a perspective view of a laterally shiftable counter shear force knee brace which embodies principles of the present invention.

The present invention provides a uniquely shiftable, counter shear force knee brace 10 which is illustrated in various manners in FIGS. 1, 3, 4 and 12. In a manner subsequently described, the brace 10 is securable to a human leg 12 (shown in phantom in FIGS. 3 and 4) having a thigh portion 14, a knee 16, and a calf portion 18. Generally speaking, the brace 10 functions to counteract anterior shifting of the tibia created by the quadriceps muscle, as the leg is extended from a flexed position (FIG. 3) toward its fully straightened position (FIG. 4), when the anterior cruciate ligament in the illustrated leg is missing or damaged.

Brace 10 includes a thigh support section comprising a pair of elongated rigid thigh support members 20 which are adapted to extend longitudinally along lateral and medial sides of the thigh 14, and a calf support section comprising a pair of elongated rigid calf support members 22 which are adapted to extend longitudinally along lateral and medial sides of the calf 18. The inner ends of the thigh and calf support member pairs 20 and 22 are pivotally interconnected by means of a pair of specially designed hinge structures 24 positioned on opposite sides of the knee 16. As will be seen, the hinges function as brace shifting means which cause various counteractive portions of the brace structure to create, in response to leg extension, a shear force across the knee which opposes that created by the quadriceps muscle. To increase the wearing comfort of the brace 10, suitable resilient padding members 26 and 28 are respectively secured to the inner sides of the thigh support members 20 and the calf support members 22 (these padding members having been deleted from FIG. 12 for illustrative clarity).

A padded, anterior femoral shell member 30 having a generally semicircular cross-section is intersecured between outer end portions of the thigh support members 20 and is adapted to rest upon the upper side of the thigh portion 14. In a similar fashion, a considerably smaller padded anterior tibial shell member 32 having a generally semicircular cross-section is intersecured between outer end portions of the calf support members 22 and is adapted to rest upon the upper side of the calf portion 18. The thigh support members 20 are secured to the thigh 14 by means of an anterior thigh support strap 34 and a posterior thigh strap network 36.

The thigh support strap 34 is covered on its opposite sides with a fastening pile material 38, and the free ends of the strap 34 are provided with complementary fastening hook material (not shown). The free ends of the strap 34 are passed through D-ring elements 40 formed integrally with the thigh support members 20, and are then secured to a central portion of the strap which, on its inner side surface carries a resilient padding member 42. An elongated plastic guard strip 44, with fastening hooks formed on its underside, is extended along the upper side of the thigh support strap 34 and removably secured to the fastening pile material 38 thereon to assist in holding the strap 34 in its tightened position.

Figure 2:
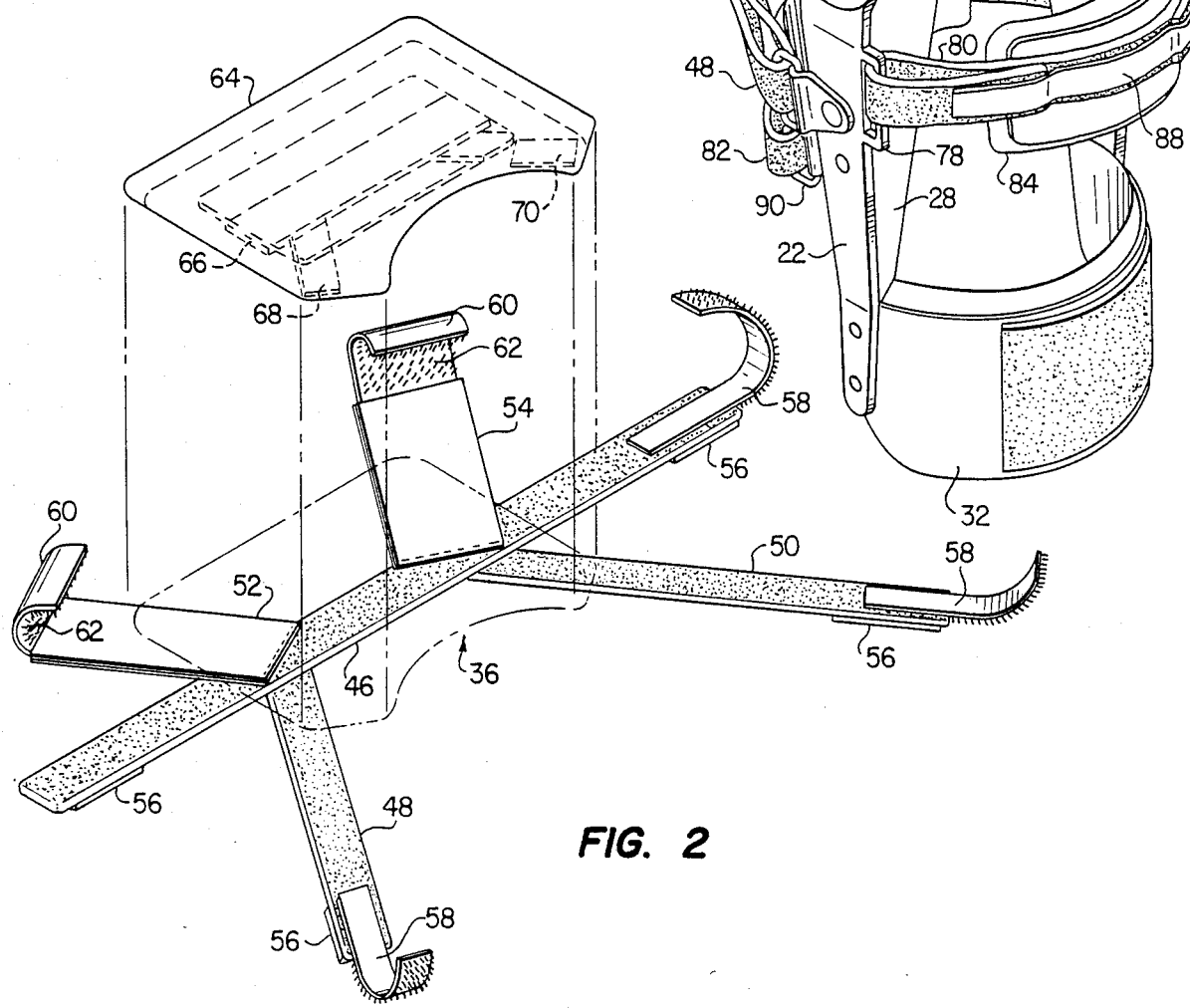
FIG. 2 is a partially exploded perspective view of a posterior stap network portion of the brace which has been removed from the balance of the brace for illustrative purposes.

Referring additionally now to FIG. 2, the posterior thigh strap network 36 includes a distal posterior thigh force strap 46, right and left control straps 48 and 50, and right and left elastic retraction straps 52 and 54. Control straps 48 and 50, like the force strap 46, are covered on their opposite sides with fastening pile material. The inner or left ends of the control straps 48 and 50 are sewn to a longitudinally intermediate portion of the force strap 46 and extend rightwardly therefrom at forwardly diverging angles. Along their lower sides, the outer ends of the straps 46, 48 and 50 are provided with strips of fastening hook material 56. The outer ends of the straps 48 and 50, and an outer end of the strap 46, are provided with fastening hook material guard strips 58 similar to the previously described guard strip 44.

The inner ends of the elastic retraction straps 52 and 54 are also sewn to a longitudinally intermediate portion of the force strap 46 and extend leftwardly or rearwardly therefrom at rearwardly diverging angles. Secured to the free ends of the elastic straps 52 and 54 are securing tab members 60 having fastening hook material 62 on their upper side surfaces. A resilient posterior thigh pad member 64 is secured to a longitudinally central portion of the force strap 46, and to inner end portions of the control straps 48 and 50, by means of appropriately positioned fastening hook material sections 66, 68 and 70 secured to the underside of the pad 64 and engaging the underlying portions of the fastening pile material on the upper sides of the straps 46, 48 and 50.

The posterior thigh strap network 36 is secured to the balance of the brace 10 to press the posterior thigh pad 64 against the underside of the thigh 14 by securing the elastic strap tab members 60 to fastening pile material 72 secured to the outer side surface of the femoral shell member 30, looping the outer ends of the thigh force strap 46 and the control straps 48, 50 respectively through D-rings 74, 76 pivotally secured to the thigh and calf support members 20, 22. The looped ends of the straps 46, 48 and 50 are then attached to longitudinally intermediate portions of their associated straps using the fastening hook material strips 56 and the guard strips 58. In this manner, all of the posterior network straps 46, 48, 50, 52 and 54 may be independently and selectively tightened relative to the balance of the brace 10 for purposes later described. As best illustrated in FIGS. 1, 3 and 4, the pivot points for the D-rings 74 are positioned longitudinally between the femoral shell member 30 and the integral D-rings 40 along the thigh support members 20, and the pivot points for the D-rings 76 are positioned just slightly to the right of integral D-rings 78 formed on the calf support members 22 just slightly forwardly of the hinges 24.

The calf support members 22 are secured to the calf 18 by means of a proximal anterior tibial force strap 80 and a posterior calf support strap 82, the straps 80, 82 are similar in construction to the previously described anterior thigh support strap 34 and have flexible support pads 84 and 86 respectively secured to longitudinally intermediate portions of their inner side surfaces. The outer ends of strap 80 are looped through the D-rings 78 and are secured to the balance of the strap by means of fastening hook sections secured to the free strap ends, and a plastic guard strip 88. In a similar manner, the outer ends of the strap 82 are looped through a pair of D-rings 90 secured to the calf support members 22, and are secured to a longitudinally intermediate portion of the strap 82 by means of fastening hook material sections on the free strap ends, and a plastic guard strip 92.

Figure 3:
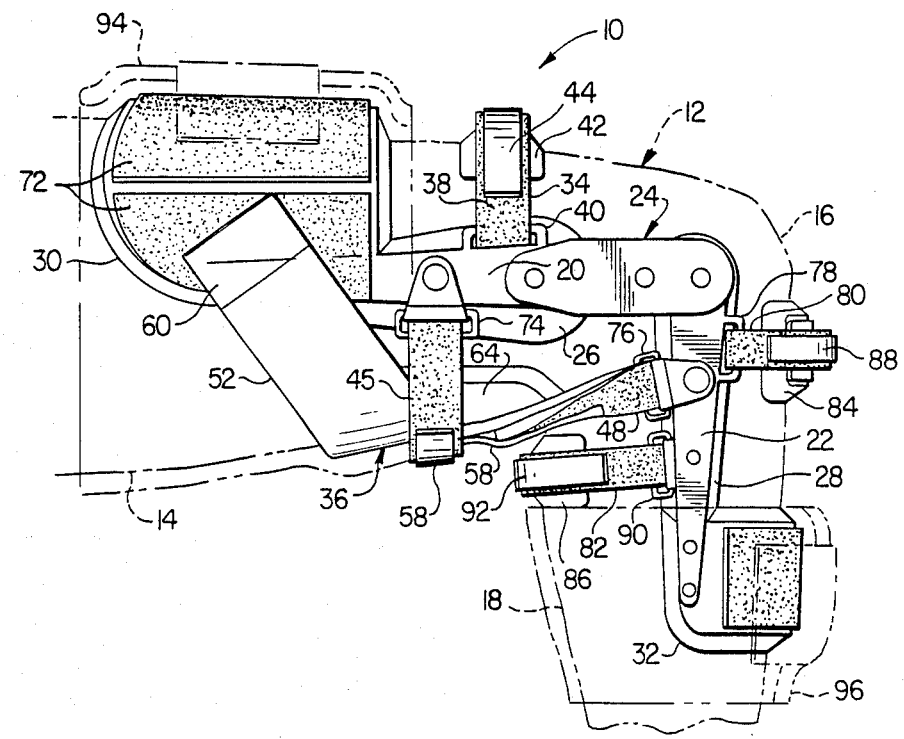
FIG. 3 is a reduced scale side elevational view of the brace operatively secured to a human leg flexed at a 90° angle and illustrated in phantom.

The brace 10 is initially installed on the leg 12 with the leg in its approximately 90° flexed position as illustrated in FIG. 3, and the various previously described straps are suitably tightened to properly align the brace on the leg. To complete the installation of the brace 10 on the leg, conventional flexible overwrap members 94 and 96 (illustrated in phantom in FIG. 3) are secured outwardly around the thigh 14 and the calf 18 over the shell members 30 and 32.

In the absence of or damage to the anterior cruciate ligament in the leg 12, extension of the leg from a flexed position illustrated in FIG. 3 toward its fully straightened position illustrated in FIG. 4, the quadriceps muscle tends to anteriorly displace the tibia, thereby creating a shear force across the knee as depicted by the dashed arrows 98 in FIG. 4.

According to a primary feature of the present invention, upon such extension of the leg 12 toward its fully straightened position, a relative anterior-posterior shift is created between the thigh support members 20 and the calf support members 22 to create an oppositely directed counter shear force across the knee 16 as represented by the solid line arrows 100 in FIG. 4 to force-fully counteract the quadriceps muscle-induced shear force and substantially prevent the undesirable anterior shifting of the tibia. As will be later seen, this very desirable artificial ligament function of the brace 10 is achieved in a unique manner which substantially prevents the brace from migrating distally along the leg 12 in response to repeated flexion and extension of the leg. The unique relative anterior-posterior shift between the thigh and calf support members 20, 22 is created by novel motion and forces imparted thereto by the hinges 24 as will now be described in detail with initial reference to FIG. 5.

Figure 5:
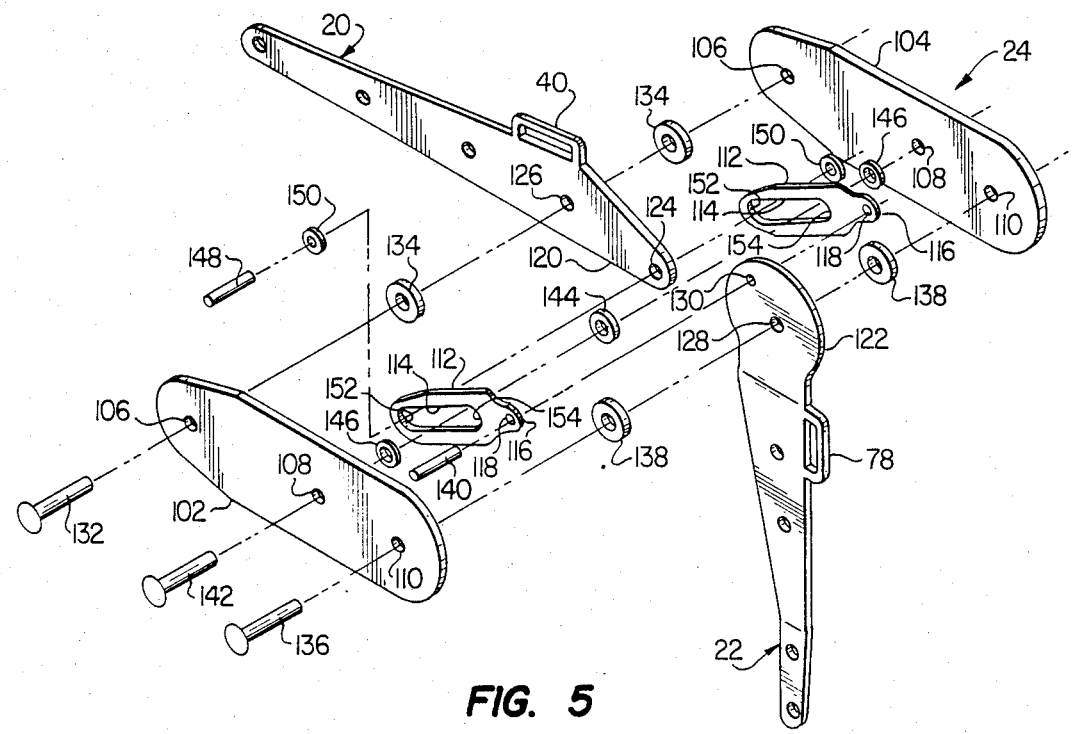
FIG. 5 is an exploded perspective view of one of the hinges used in the brace, and the thigh and calf support members which the hinge pivotally interconnects.
Figure 8:
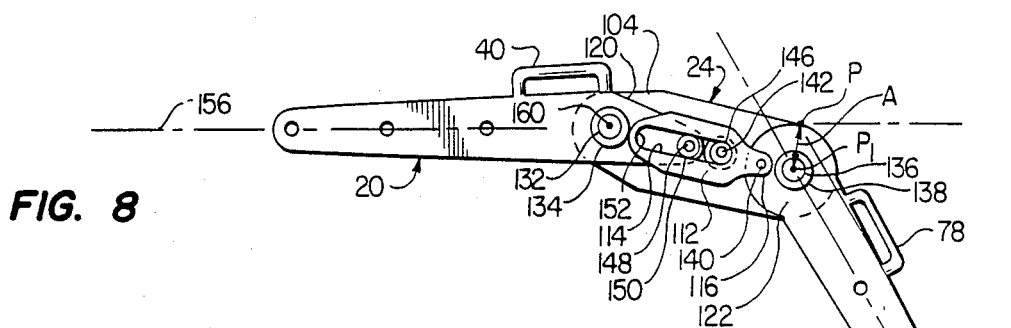

Each of the hinges 24 comprises elongated outer and inner side cover plates 102 and 104 having aligned small circular openings 106, 108 and 110 respectively formed through left end portions, longitudinally intermediate portions, and right end portions of the coverplates as viewed in FIG. 5. Each of the hinges also includes a pair of elongated drive plate members 112 having elongated slots 114 formed therethrough and extending rightwardly from adjacent their left ends, and narrowed right end portions 116 having small circular openings 118 formed therethrough, the drive plate members 112 being sandwiched between the coverplates 102 and 104. As illustrated in FIG. 5, the facing inner end portions 120 and 122 of an associated pair of thigh and calf support members 20 and 22 are sandwiched between the drive plate members 112. Inner end portion 120 is longitudinally tapered, and is provided with a small circular opening 124 adjacent its right end, and a small circular opening 126 positioned generally beneath the right end of the integral D-ring 40. Inner end portion 122 has a generally circular configuration, and is provided with a small circular central opening 128 and a small circular opening 130 adjacent its periphery.

The illustrated thigh support member 20 in FIG. 5 is pivotally connected to the cover plates 102, 104 by means of a rivet 132 which is extended through the cover plate openings 106 and the thigh support member opening 126 and a pair of spacing washers 134 positioned between the coverplates on opposite sides of the thigh support member. In a similar fashion, the illustrated calf support member 22 is pivotally secured to the cover plates by means of a rivet 136 which is extended through the cover plate openings 110, the calf support member opening 128, and a pair of spacing washers 138 positioned between the cover plates on opposite sides of the calf support member inner end portion 122.

The right end portions 116 of the drive plate members 112 are pivotally secured to opposite sides of the calf support member inner end portion 122 by means of a pivot pin 140 which is captively retained between the coverplates 102,, 104 and extends through the drive plate member openings 118 and the peripheral opening 130 in the inner end portion 122 of the calf support member 22.

The cover plate members 102, 104 are further intersecured by a rivet 142 which extends through the central coverplate openings 108, the drive plate member slots 114, a spacing washer 144 positioned between the drive plate members, and a pair of drive bushings or guide members 146 which are slidably carried in the slots 114. To the left of the pin 140 is a pivot pin 148 which is captively retained between the coverplates 102, 104 and extends through the drive plate member slots 114 and the circular opening 124 at the inner end of the thigh support member 20. Mounted on the opposite ends of the pin 148 are a pair of drive bushings or guide members 150 that are slidably carried in the drive plate member slots 114 to the left of the drive bushings 146. The left and right ends 152 and 154 of the drive plate member slots 112 are circularly curved and respectively operate as stops for the drive bushings 150 and 146 in a manner subsequently described.

The hinge and support member structure illustrated in exploded fashion in FIG. 5 is elevationally depicted in an assembled state in FIGS. 6–11, the outer cover plate member 102 having been removed for illustrative clarity. FIGS. 6–11 sequentially illustrate the workings of the hinge components as the thigh and calf support members 20, 22 are moved from their fully flexed position shown in FIG. 6 through a straightened position shown in FIG. 10, to a hyperextended position shown in FIG. 11. With the thigh and calf support members 20, 22 in their flexion limit position depicted in FIG. 6, the longitudinal axes 156, 158 of the support members 20, 22 form an acute angle with one another, and further flexion movement between the support members 20, 22 is prevented by the interengagement of the drive bushings 150 with the left ends 152 of the drive member slots 114, and the interengagement between the spacing washers 138 and the right ends of the drive members 112. The thigh support member 20 is pivotable relative to the support plates 102, 104 about a pivot axis 160 extending through the rivet 132. The calf support member 22 is pivotable relative to the support plates about a pivot axis P the thigh support member longitudinal axis 156.

To simplify the description of the relative anterior-posterior shift between the thigh and calf support members 20, 22 caused by the operation of the hinge 24, it will be assumed that the thigh support member 20 is held stationary so that the entire resulting shift between the two support members occurs in the calf support member 22. However, it will be readily appreciated that during actual operation of the brace 10 this relative anterior-posterior shift is a portioned between the thigh and calf support members at each of the hinges 24.

As the calf support member 22 is pivoted in a counterclockwise direction from its fully flexed position shown in FIG. 6 toward its 90° flexion position shown in FIG. 7 (such 90° flexion position corresponding to the brace orientation shown in FIG. 3), the drive members 112 are forced downwardly and leftwardly relative to the drive bushings 146 and 150 so that when the calf support member 22 reaches its 90° flexion position the drive bushings 146 and 150 are positioned considerably closer to the right ends 154 of the drive member slots 114. The original pivot axis P between the calf support member and the coverplates 102, 104 remains in its original position in which it intersects the longitudinal axis 156 of the thigh support member 20.

As the calf support member 22 is further pivoted in a counterclockwise direction through a 75° flexion angle toward its 60° flexion position (FIG. 8) the drive bushings 146 bottom out against the right ends 154 of the drive member slots 114. This bottoming out prevents further leftward translation of the drive members 112 relative to the drive bushings and translates the original pivot axis P downwardly through a clockwise arc A, centered about the pivot axis 160, to a shifted position $P_1$. This shift of the pivot axis P causes a corresponding posterior shift of the longitudinal calf support member axis from its original orientation 158 relative to the original pivot axis P to a new position $158_a$ illustrated in FIG. 8.

Figure 9:
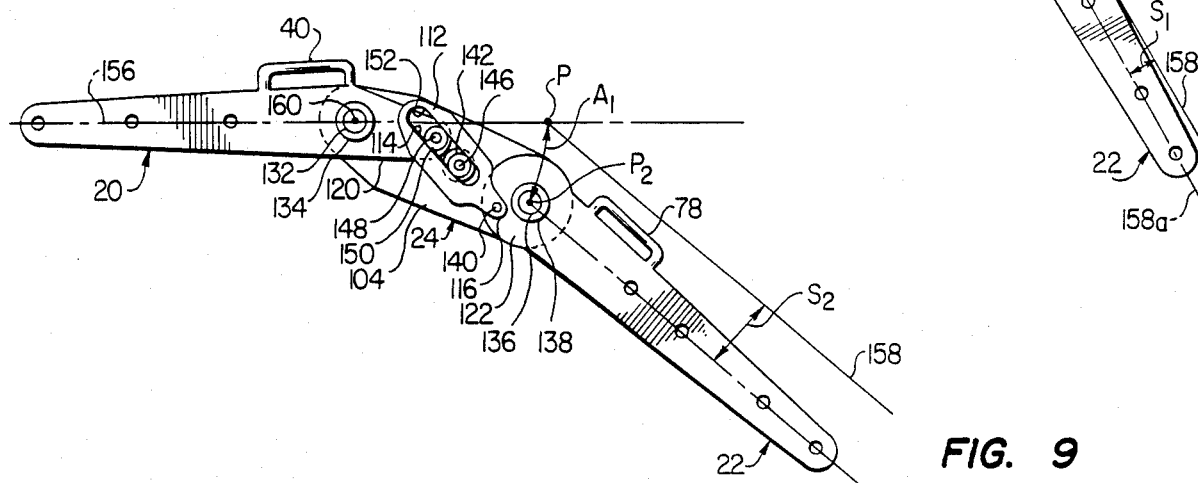
Figure 10:
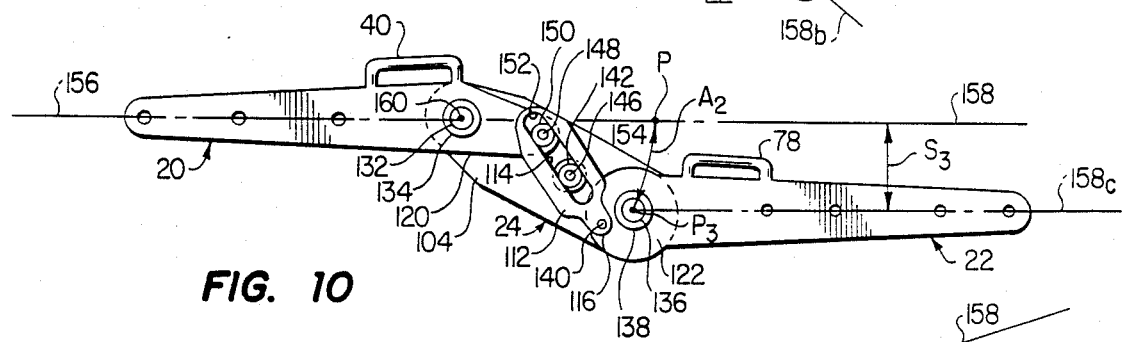

Further counterclockwise movement of the calf support member 22 to its 40° flexion angle illustrated in FIG. 9 increases the arc distance A to an arc distance $A_1$ which further shifts the longitudinal calf support member axis through a total posterior distance $S_2$ to a new relative orientation $158_b$. During this calf support member pivotal motion between its 60° flexion angle (FIG. 8) to its 40° flexion angle (FIG. 9) the drive plate members 112 have been pivoted in a clockwise direction and have been moved downwardly and rightwardly relative to the drive bushings 146 and 150 which are slidably carried within the drive plate slots 114.

Further counterclockwise pivoting of the calf support member 22 to the "straightened" position of the support members 20, 22 (corresponding to the brace position depicted in FIG. 4) increases the arc $A_1$ to an arc $A_2$, move the pivot axis of the calf support member to a new position $P_3$ relative to its position $P_2$ in FIG. 9, and further shifts the longitudinal calf support member axis to a position $158_c$ relative to its original position 158 to thereby increase the lateral calf support member shift distance to $S_3$.

Figure 11:
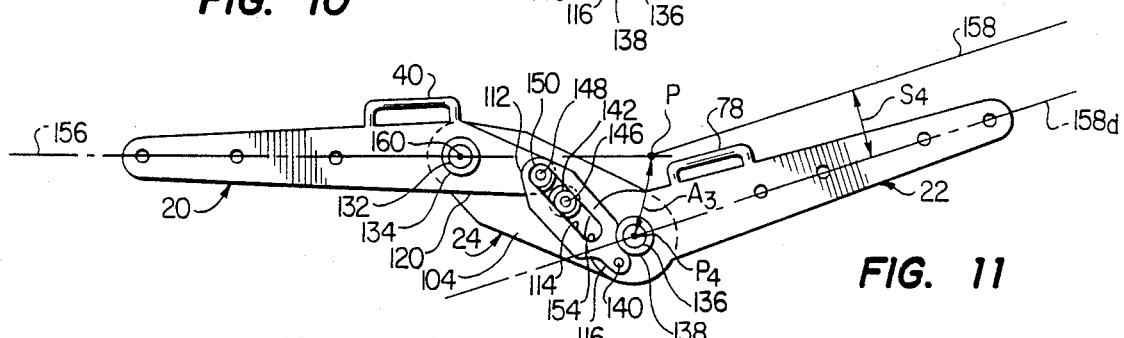
Figure 12:
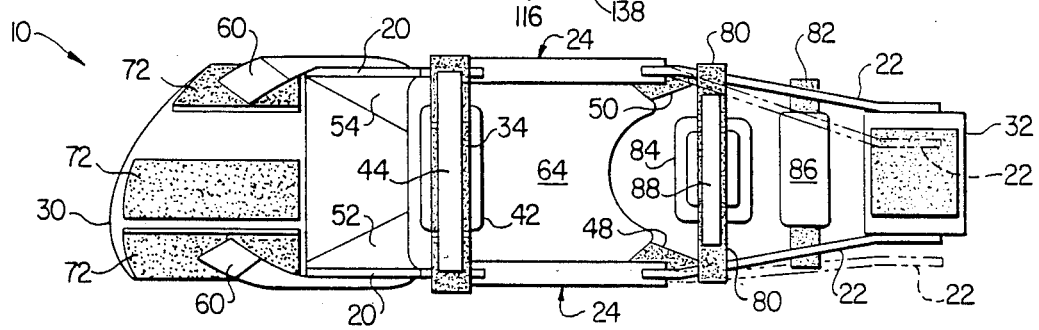
FIG. 12 is a reduced scale top plan view of the brace in its straightened position as shown in FIG. 4.

Finally, further counterclockwise pivoting of the calf support member 22 to its hyperextended position depicted in FIG. 11 causes the drive bushings 150 to bottom out in the left ends 152 of the drive member slots 114 to prevent further counterclockwise pivoting of the calf support member 22 relative to the thigh support member 20. This final counterclockwise pivoting of the calf support member 22 causes a slight anterior lateral shifting of the calf support member to reduce the arc $A_2$ to an arc $A_3$, shift the calf support member pivot axis from point $P_3$ to point $P_4$ relative to its original location P, and laterally shift the longitudinal calf support member axis to a location $158_d$ which correspondingly reduces the lateral shift distance $S_3$ (FIG. 10) to a total lateral shift distance $S_4$.

It can readily be seen that this relative anterior-posterior shift between the thigh and calf support members 20, 22 creates in the brace 10, via the posterior pad 64, the anterior pad 84 and the anterior thigh shell 30, the counter shear force 100 across the knee 16 (FIG. 4) which counteracts the opposite shearforce 98 created by the quadriceps muscle. As is well known, in the absence of or damage to the anterior cruciate ligament, the quadriceps muscle creates the undesirable anterior shift of the tibia as the leg, while being extended, reaches a flexion angle of approximately 40°. As the leg is further extended, this anterior tibial shifting force, which creates the shear force 98 across the knee 16, increases as the leg approaches its fully extended position. This quadriceps muscleinduced anterior shifting of the tibia is greatly reduced when the leg is between its fully flexed position and the aforementioned flexion angle of approximately 40°.

As just described, the operation of the hinges 24 initiates the relative lateral shifting between the thigh support and calf support members 20, 22 somewhat before this 40° flexion angle is reached–initiating the anterior-posterior support member shift at approximately 75° flexion (prior to which the positional relationship between the thigh and calf support members closely corresponds to the femur-tibia positional relationship). This "pre-start" initiation of the lateral brace shift is designed to compensate for soft tissue "give" in the leg so that when the leg reaches the 40° flexion position the counter shear force created by the brace is effectively transferred to both the femur and the tibia. Accordingly, it can readily be seen that the brace 10 of the present invention very closely tracks, in a reverse sense, the actual shear force 98 across the knee 16 created by the quadriceps muscle as the leg 12 is extended from, for example, its 90° flexion position depicted in FIG. 3 to its fully straightened position depicted in FIG. 4.

Like the hinges 24 just described, the strap system used to secure the brace 10 to the leg 12 provides the brace with a variety of operational advantages over conventional knee braces used to artificially replace or supplement the anterior cruciate ligament. For example, according to another important aspect of the present invention, the posterior strap network 36 uniquely functions to substantially prevent distal migration of the brace 10 along the leg 12 in response to extension and flexion of the leg.

Referring to FIGS. 3 and 4, it can be seen that as the leg 12 is extended from its 90° flexion position (FIG. 3) to its fully straightened position (FIG. 4) the D-rings 76, to which the outer ends of the control straps 48, 50 are secured, are caused to move upwardly and forwardly. The forward movement of these D-rings 76 creates an increased tension force in the control straps 48, 50 and moves the posterior thigh pad member 64 forwardly along the posterior side of the thigh 14 as the leg is extended. This forward movement of the thigh pad 64 also pivots the force strap 46 in a counterclockwise direction and stretches the elastic straps 52.

This unique forward movement of the thigh pad 64, which may easily be seen by comparing FIGS. 3 and 4, forwardly shifts the posterior fulcrum point of the strap network 36, and mimics the stretching of the skin and muscle of the posterior thigh, and has been found in developing the brace 10 to substantially preclude distal migration of the brace in response to flexion and extension of the leg. As the leg 12 is flexed from its FIG. 4 position to its FIG. 3 position, the stretched elastic straps 52 function to assist in pulling the thigh pad 64 and the force strap 46 back to their FIG. 3 positions Further brace operational flexibility is provided by the control straps 48 and 50 which serve, together with the other previously described network straps, to interconnect the posterior network 36 between the thigh and calf support members 20, 22. For example, by appropriate tightening or loosening the control straps 48, 50, both the initiation and degree of the beneficial forward shifting of the thigh pad 64 can be precisely controlled. Specifically, by loosening the control straps 48, 50 when the brace 10 is initially installed on the leg in its 90° flexion position, the flexion angle at which forward thigh pad shifting is initiated is decreased. Conversely, by tightening the control straps, forward shifting of the thigh pad 64 is initiated at a greater leg flexion angle as the leg is being extended.

Additionally, by differentially tightening the control straps 48 and 50, the calf support members may be caused to shift or flex to the right or left relative to the thigh support members 20 as the leg is extended. This is quite useful in inhibiting lateral tibial shift in the opposite direction when this particular counteractive force is desirable. As an example, and referring now to FIG. 12, if the tibia of leg 12 is subject to an undesirable medial shift upon leg extension, the right control strap 48 is simply tightened to a greater degree than the left control strap 50 when the brace is initially installed on a leg in its 90° flexion position. As the leg is then extended, the tighter right control strap exerts a rearward pulling force on the right calf support member 22 before a similar rearward pulling force is exerted on the left calf support member 22 by the left control strap 50.

This differential tightening of the control straps causes a rightward or lateral shift of the calf support members 22 (to their dotted line positions depicted in FIG. 12) as the leg is extended further and further toward its fully straightened position. As the leg is subsequently flexed, the differential pulling force exerted on the calf support members 22 by the differentially tightened control straps 48, 50 is relaxed, and the calf support members 22 are returned to their original solid line orientations relative to the hinges 24 and the thigh support members 20. If a medial shift or flex of the calf support members is desired in response to leg extension, the left control strap 50 is simply tightened more than the right control strap when the brace is initially attached to the leg in its 90° flexion position.

The level of the counteractive shear force 100 (FIG. 4) exerted across the knee 16 in response to extension of the leg 12 may be precisely controlled simply by appropriate tightening or loosening of the anterior tibial force strap 80. Specifically, the tighter the force strap 80 is made when the brace is initially attached to the leg, the greater the resulting counter shear force 100, and vice versa.

Another significant advantage provided by the brace 100 is that it is designed to be installed, as previously described, with the leg in an approximately 90° flexion position in contrast to conventional knee braces of this general type which must be installed with the leg in a fully extended position. Because of this installation feature, excessive loosening of the strap system when the leg is flexed to its 90° position may be positively avoided. Thus, even with the leg in a nearly fully flexed position, the brace 10 guards against undesirable anterior tibial displacement.

To summarize, the brace 10 of the present invention is uniquely operative to create the counter shear force 100 across the knee 16 in a manner which very closely tracks, in a reverse sense, the quadriceps muscle-induced shearforce 98 across the knee. This essentially "mirror image" counter shear force is achieved in the brace 10 essentially without the conventional problem of distal brace shift along the leg, caused by leg extension and flexion, by virtue of the unique operation of the posterior strap network 36 which longitudinally shifts and then repositions the thigh pad 64 in response to leg extension and flexion, respectively. The relative lateral shifting between the thigh and calf support members 20, 22 by virtue of the operation of the hinges 24 is supplemented by the ability to simultaneously create a lateral or medial shift of the calf support members 22 relative to the hinges and the thigh support members by differentially tightening the control straps.

The foregoing detailed description is to be clearly understood as being given by way of illustration and example only, the spirit and scope of the present invention being limited solely by the appended claims.

What is claimed is:

1. A knee brace, connectable to a human leg having thigh, knee and calf portions, for compensating for loss of or damage to the anterior cruciate ligament of the leg by creating a counteractive anterior-posterior shear force across the knee which opposes an oppositely directed anterior-posterior shear force across the knee generated by the quadriceps muscle of the leg during leg extension, and tending to cause an anterior shift of the tibia relative to the femur, said knee brace comprising:

first and second elongated rigid thigh support members positionable to longitudinally extend lengthwise along the lateral and medial sides of the thigh with inner end portions of the thigh support members positioned adjacent the knee;

first and second elongated rigid calf support members positionable to longitudinally extend lengthwise along the lateral and medial sides of the calf with inner end portions of the calf support members positioned adjacent the knee;

attachment means for firmly attaching said thigh and calf support members to the thigh and calf, respectively, for movement therewith, and for transmitting to the thigh and calf anteriorly and posteriorly directed forces imposed on said thigh and calf support members; and first and second hinge means, each having a plurality of pivot axes, said first and second hinge means being positionable on opposite sides of the knee for pivotally connecting said inner end portions of said thigh support members to said inner end portions of said calf support members, said first and second hinge means being operative to create a relative anterior-posterior shift between said thigh and calf support members, in response to extension of the leg, in a manner causing said attachment means to generate said counteractive shear force.

2. The knee brace of claim 1 wherein said thigh and calf support members have outer end portions and said attachment means include:

a generally semicircular anterior femoral shell member interconnected between said outer end portions of said first and second thigh support members, an adjustably tightenable anterior thigh support strap positioned between said anterior femoral shell member and said first and second hinge means, and interconnected between said first and second thigh support members, a generally semicircular anterior tibial shell member interconnected between said outer end portions of said first and second calf support members, an adjustably tightenable anterior tibial force strap positioned between said first and second hinge means and said anterior tibial shell member, and interconnected between said first and second calf support members, an adjustably tightenable posterior calf support strap positioned between said first and second hinge means and said anterior tibial shell member, and interconnected between said first and second calf support members, and a posterior strap network interconnected between said thigh support members and said calf support members and including an adjustably tightenable posterior thigh force strap interconnected between said first and second thigh support members and positioned between said anterior femoral shell and said first and second hinge means.

3. A knee brace, connectable to a human leg having thigh, knee and calf portions, for compensating for loss of or damage to the anterior cruciate ligament of the leg by creating a counteractive anterior-posterior shear force across the knee which opposes an oppositely directed anterior-posterior shear force across the knee generated by the quadriceps muscle of the leg during leg extension and tending to cause an anterior shift of the tibia relative to the femur, said knee brace comprising:
- first and second elongated rigid thigh support members having outer end portions and being positionable to longitudinally extend lengthwise along the lateral and medial sides of the thigh with inner end portions of the thigh support members positioned adjacent the knee;
- first and second elongated rigid calf support members having outer end portions and being positionable to longitudinally extend lengthwise along the lateral and medial sides of the calf with inner end portions of the calf support members positioned adjacent the knee;
- attachment means for firmly attaching said thigh and calf support members to the thigh and calf, respectively, for movement therewith, and for transmitting to the thigh and calf anteriorly and posteriorly directed forces imposed on said thigh and calf support members, said attachment means including:
  - a generally semicircular anterior femoral shell member interconnected between said outer end portions of said first and second thigh support members,
  - an adjustably tightenable anterior thigh support strap positioned between said anterior femoral shell member and said first an second hinge means, and interconnected between said first and second thigh support members,
  - a generally semicircular anterior tibial shell member interconnected between said outer end portions of said first and second calf support members,
  - an adjustably tightenable anterior tibial force strap positioned between said first and second hinge means and said anterior tibial shell member, and interconnected between said first and second calf support members,
  - an adjustably tightenable posterior calf support strap positioned between said first and second hinge means and said anterior tibial shell member, and interconnected between said first and second calf support members, and
  - a posterior strap network interconnected between said thigh support members and said calf support members and including an adjustably tightenable posterior thigh force strap interconnected between said first and second thigh support members and positioned between said anterior femoral shell and said first and second hinge means, said posterior strap network further including a first adjustably tightenable control strap interconnected between said posterior thigh force strap and said first calf support member, and a second adjustably tightenable control strap interconnected between said posterior thigh force strap and said second calf support member; and
- first and second hinge means, postionable on opposite sides of the knee for pivotally connecting said inner end portions of said thigh support members to said inner end portions of said calf support members, and for creating a relative anterior-posterior shift between said thigh and calf support members, in response to extension of the leg, in a manner causing said attachment means to generate said counteractive shear force.

4. The knee brace of claim 3 wherein said posterior strap network further includes:

first and second elastic straps interconnected between said posterior thigh force strap and opposite side portions of said anterior femoral shell member.

5. A knee brace, connectable to a human leg having thigh, knee and calf portions, for compensating for loss of or damage to the anterior cruciate ligament of the leg by creating a counteractive anterior-posterior shear force across the knee which opposes an oppositely directed anterior-posterior shear force across the knee generated by the quadriceps muscle of the leg during leg extension and tending to cause an anterior shift of the tibia relative to the femur, said knee brace comprising:
- first and second elongated rigid thigh support members having outer end portions and being positionable to longitudinally extend lengthwise along the lateral and medial sides of the thigh with inner end portions of the thigh support members positioned adjacent the knee;
- first and second elongated rigid calf support members having outer end portions and being positionable to longitudinally extend lengthwise along the lateral and medial sides of the calf with inner end portions of the calf support members positioned adjacent the knee;
- attachment means for firmly attaching said thigh and calf support members to the thigh and calf, respectively, for movement therewith, and for transmitting to the thigh and calf anteriorly and posteriorly directed forces imposed on said thigh and calf support members; and
- first and second hinge means, positionable on opposite sides of the knee for pivotally connecting said inner end portions of said thigh support members to said inner end potions of said calf support members, and for creating a relative anterior-posterior shift between said thigh and calf support members, in response to extension of the leg, in a manner causing said attachment means to generate said counteractive shear force, each of said first and second hinge means including:
  - a pair of cover plate members positioned on opposite sides of the inner end portions of an associated pair of thigh and calf support members,
  - means for pivotally connecting the inner end portions of said associated pair of thigh and calf support members, respectively, to said cover plate members at first and second pivot points spaced apart from one another,
  - elongated drive plate means, positioned between said cover plate members, for creating said relative anterior-posterior shift, said drive plate means having first and second end portions and a longitudinally extending slot positioned between said first and second end portions of said drive plate means,
  - means for pivotally connecting said first end portion of said drive plate means to said inner end portion of the calf support member of said associated pair of thigh and calf support members at a third pivot point spaced apart from said second pivot point,
  - a first guide member fixedly supported between said cover plate members, positioned between the inner end portions of said associated pair of thigh and calf support members, and slidably positioned in said slot, and a second guide member anchored to the inner end portion of the thigh support member of said associated pair of thigh and calf support members inwardly of said first pivot point and slidably positioned in said slot.

6. Knee brace apparatus for use in counteracting leg muscle force-induced abnormal relative displacement between the femur and tibia portions of a human leg having an angular flexion range with first and second portions, said abnormal relative displacement occurring at least primarily while the leg is in said first portion of its angular flexion range, said knee brace apparatus comprising:

a first support section securable to a thigh portion of the leg and having a first counteractive portion;

a second support section securable to a calf portion of the leg and having a second counteractive portion, said first and second support sections being pivotally interconnected; and brace shifting means for varying the relative movement between said first and second counteractive portions, during pivotal leg movement about the knee, in a manner such that:

as the leg is moved within said second portion of its angular flexion range the relative movement between said first and second counteractive portions closely corresponds to the relative movement between the femur and tibia, and as the leg is moved within said first portion of its angular flexion range the relative movement between said first and second counteractive portions is altered to cause them to exert a shifting force on the leg which counteracts and inhibits said abnormal relative displacement between its femur and tibia portions, said brace shifting means being operative, when the leg is in said first portion of its angular flexion range, to cause said shifting force to create an anterior-posterior shear force across the knee joint of the leg by creating an anterior shift of said first support section and posterior shift of said second support section.

7. The knee brace apparatus of claim 6 wherein said first portion of said angular flexion range includes an angular flexion range extending between approximately 40° and approximately 0°.

8. The knee brace apparatus of claim 6 wherein said first portion of said angular flexion range includes an angular flexion range extending between approximately 75° and approximately 0°.

9. The knee brace apparatus of claim 6 wherein:
said first and second support sections are pivotally connected by hinge means, and
said brace shifting means are incorporated in said hinge means.

10. The knee brace apparatus of claim 6 wherein said first and second counteractive portions of said first and second support sections respectively include:
adjustably tightenable first strap means for securing said first support section to the thigh and transmitting an anteriorly directed brace shifting force to the posterior side of the thigh in response to extension of the leg, and
adjustably tightenable second strap means for securing said second support section to the calf and transmitting a posteriorly directed brace shifting force to the anterior side of the calf in response to extension of the leg.

11. The knee brace apparatus of claim 10 wherein:
said first strap means are operative to transmit said anteriorly directed brace shifting force to said posterior side of the thigh at a location thereon which varies in response to leg extension and flexion in a manner inhibiting distal migration of the knee brace apparatus along the leg.

12. Knee brace apparatus for use in counteracting leg muscle force-induced abnormal relative displacement between the femur and tibia portions of a human leg having an angular flexion range with first and second portions, said abnormal relative displacement occurring at least primarily while the leg is in said first portion of its angular flexion range, said knee brace apparatus comprising:

a first support section securable to a thigh portion of the leg and having a first counteractive portion;

a second support section securable to a calf portion of the leg and having a second counteractive portion, said first and second support sections being pivotally interconnected, said first and second counteractive portions of said first and second support sections respectively including:

adjustably tighenable first strap means for securing said first support section to the thigh and transmitting an anteriorly directed brace shifting force to the posterior side of the thigh in response to extension of the leg, and adjustably tightenable second strap means for securing said second support section to the calf and transmitting a posteriorly directed brace shifting force to the anterior side of the calf in response to extension of the leg; and brace shifting means for varying the relative movement between said first an second counteractive portions, during pivotal leg movement about the knee, in a manner such that:

as the leg is moved within said second portion of its angular flexion range the relative movement between said first and second counteractive portions closely corresponds to the relative movement between the femur and tibia, and as the leg is moved within said first portion of its angular flexion range the relative movement between said first and second counteractive portions is altered to cause them to exert a shifting force on the leg which counteracts and inhibits said abnormal relative displacement between its femur and tibia portions, said first strap means being interconnected between said first and second support sections and being adjustably operative to selectively cause lateral or medial flexure of said second support section relative to said first support section in response to extension of the leg.

13. The knee brace apparatus of claim 10 wherein:
said second strap means are adjustable to selectively vary the magnitude of said posteriorly directed brace shifting force.

14. A knee brace connectable to a human leg having thigh, knee and calf potions, said knee brace being operative in response to leg flexion to create across the knee portion of the leg a counteractive shear force in opposition to the shear force across the knee portion caused by the quadriceps muscle of the leg, said knee brace comprising:

a first support section securable to said thigh portion for movement therewith, said first support section having opposite side portions and an outer end portion;

a second support section securable to said calf portion for movement therewith;

attachment means for operatively securing said first and second support sections to said thigh and calf portions and for transmitting received anterior and posterior forces to said thigh and calf portions;

hinge means for pivotally interconnecting said first and second support sections and, in response to leg extension, for respectively exerting anterior and posterior forces on said first and second support sections in a manner causing said attachment means to create said counteractive shear force on the leg; and distal migration inhibiting means, associated with said attachment means and interconnected between said first and second support sections, for inhibiting distal migration of said knee brace along the leg, in response to extension and flexion thereof, by varying in a predetermined manner the location of an anterior attachment means force transmitted to said thigh portion in response to extension and flexion of the leg, said distal migration inhibiting means including:

an adjustably tightenable posterior thigh force strap interconnected between said opposite side portions of said first support section and positioned between said hinge means and the outer end of said first support section, adjustably tightenable control strap means interconnected between said posterior thigh force strap and said second support section, and elastic strap means interconnected between said posterior thigh force strap and the outer end portion of said first support section.

15. A knee brace connectable to a human leg having thigh, knee and calf portions, said knee brace being operative in response to leg flexion to create across the knee portion of the leg a counteractive shear force in opposition to the shear force across the knee portion caused by the quadriceps muscle of the leg, said knee brace comprising:

a first support section securable to said thigh portion for movement therewith, said first support section having opposite side portions and an outer end portion;

a second support section securable to said calf portion for movement therewith;

attachment means for operatively securing said first and second support sections to said thigh and calf portions and for transmitting received anterior and posterior forces to said thigh and calf portions;

hinge means for pivotally interconnecting said first and second support sections and, in response to leg extension, for respectively exerting anterior and posterior forces on said first and second support sections in a manner causing said attachment means to create said counteractive shear force on the leg; and distal migration inhibiting means, associated with said attachment means and interconnected between said first and second support sections, for inhibiting distal migration of said knee brace along the leg, in response to extension and flexion thereof, by varying in a predetermined manner the location of an anterior attachment means force transmitted to said thigh portion in response to extension and flexion of the leg, said first and second support sections including a pair of elongated rigid thigh and calf support members positionable to longitudinally extend lengthwise along said thigh and calf portions, said thigh and calf support members having inner end portions, and said hinge means including a hinge structure comprising:

a pair of cover plate members positioned on opposite sides of the inner end portions of said thigh and calf support members, means for pivotally connecting the inner end portions of said thigh and calf support members, respectively, to said cover plate members at first and second pivot points spaced apart from one another, elongated drive plate means, positioned between said cover plate members, for creating a relative anterior-posterior shift between said thigh and calf support members in response to leg extension, said drive plate means having first and second end portions and a longitudinally extending slot positioned between said first and second end portions of said drive plate means, means for pivotally connecting said first end portion of said drive plate means to said inner end portion of the calf support member at a third pivot point spaced apart from said second pivot point, a first guide member fixedly supported between said cover plate members, positioned between the inner end portions of said thigh and calf members, and slidably positioned in said slot, and a second guide member anchored to the inner end portion of the thigh support member inwardly of said first pivot point and slidably positioned in said slot.

16. A knee brace connectable to a human leg having thigh, knee and calf portions, said knee brace comprising:

first and second elongated thigh support members positionable to longitudinally extend lengthwise along the lateral and medial sides of the thigh portion, respectively, with inner end portions of the thigh support members positioned adjacent the knee;

first and second elongated calf support members positionable to longitudinally extend lengthwise along the lateral and medial sides of the calf portion, respectively, with inner end portions of the calf support members positioned adjacent the knee;

first attachment means for firmly securing said thigh support members to the thigh portion for movement therewith;

second attachment means for firmly securing said calf support members to the calf portion for movement therewith;

first hinge means for pivotally interconnecting the inner end portions of said first thigh and calf support members;

second hinge means for pivotally interconnecting the inner end portions of said second thigh and calf support members; and adjustable means, interconnected between said thigh support members and said calf support members, for causing flexure of said calf support members in a selected lateral or medial direction in response to extension of the leg from a flexed position thereof.

17. The knee brace of claim 16 wherein said adjustable means include:

first and second adjustably tightenable control straps, and means for connecting said first control strap between said first thigh and calf support members, and for connecting said second control strap between said second thigh and calf support members.

18. The knee brace of claim 16 wherein said means for connecting include:

an adjustably tightenable posterior thigh force strap connected between said first and second thigh support members, said first and second control straps being respectively connected between said posterior thigh force strap and said first and second calf support members.

* * * * *